(12) United States Patent
Gressel

(10) Patent No.: US 6,629,038 B1
(45) Date of Patent: Sep. 30, 2003

(54) METHOD AND SYSTEM FOR IDENTIFYING COMMERCIALLY DISTRIBUTED ORGANISMS

(75) Inventor: Jonathan Gressel, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/655,960

(22) Filed: Sep. 5, 2000

(51) Int. Cl.$^7$ .................. G01N 33/48; C12Q 1/68; C12P 19/34; C12N 15/00; C12N 15/09; C12N 15/74

(52) U.S. Cl. .................. 702/19; 435/6; 435/91.1; 435/320.1; 435/471; 536/23.1

(58) Field of Search .................. 536/23.1, 24.33; 435/320.1, 91.1, 471, 6; 702/19

(56) References Cited

PUBLICATIONS

Adams et al. Science, vol. 252, Jun. 21, 1991, pp. 1651–1656.*

Stratagene Product Catalog (published by Stratagene, 11011 North Torrey Pines Road La Jolla, CA 92037), 1993, pp. 26, 151 and 300.*

Boguski et al. Nature Genetics, vol. 4, Aug. 1993, pp. 332–333.*

Shizuya et al., Proc. Natl. Acad. Sc. USA, vol. 89, pp. 8794–8797, Sep. 1992.*

Monaco et al., Trends in Biotechnology, vol. 12, pp. 280–284, 1994.*

Boehringer Mannheim, Boehringer Mannheim Biochemicals Catalog, 1994.*

\* cited by examiner

*Primary Examiner*—John S. Brusca
*Assistant Examiner*—Shubo Zhou
(74) *Attorney, Agent, or Firm*—G. E. Ehrlich Ltd

(57) ABSTRACT

A method of marking individuals of commercially distributed organism or organisms and offspring thereof is disclosed. The method is effected by genetically marking a plurality of individuals of the organism or organisms with a plurality of unique DNA sequences, each of the unique DNA sequences includes a variable region, so as to produce artificial, inherited and detectable genetic variability among the plurality of individuals of the commercially distributed organism or organisms.

19 Claims, 1 Drawing Sheet

METHOD AND SYSTEM FOR IDENTIFYING COMMERCIALLY DISTRIBUTED ORGANISMS

FIELD AND BACKGROUND OF THE INVENTION

The present invention relates to a method and system for identifying commercially distributed organisms and/or offspring thereof. More particularly, the present invention relates to (i) genetically marked organisms; and (ii) a database server and a method for assigning sequences to be used to genetically mark organisms and for book keeping data pertaining to the genetically marked organisms and/or their owner, producer or source.

There are a variety of reasons to have organisms tagged with an "easy to read" code. Such reasons, include, but are not limited to, (i) recognition of source; (ii) ownership; (iii) regulation; and (iii) liability.

For example, valuable bacterial or fungal strains, crop varieties, or animal strains need be identifiable for effectively effecting intellectual property (IP) rights or proof of ownership, as well as identity preservation.

Transgenic organisms bacterial or fungal strains, crop varieties, or animal strains need by identifiable for recognition of source.

In addition, regulatory authorities and various consumer groups are demanding labeling of certain transgenic commodities. They spend vast sums typically probing for common used promoters (35S, actin enhancer) or selectable marker genes (kanamycin or hygromycin resistance) and not for the trait genes, in an effort to save. Even when transgenics are discovered by such "kits", there is no information as to source. Thus, regulatory authorities may wish to consider simple, common recognition sequences for detecting transgenics.

Organisms which serve as biocontrol agents should be tagged for reasons of liability. It will be appreciated in this respect that the use of live organisms to control weed, bacterial, fungal, or insect pests is increasing. Many of the agents are closely related to known pathogens or pests and there have already been claims that a biocontrol organism changed its host range and attacked valuable species. In all probability, the related species was the culprit. There are few easy methods to ascertain causality with accuracy in some cases. There are also fears that biocontrol agents will mutate or introgress with other organisms, and there are needs to know whether the biocontrol agent changed host range (with consequences of liability) or whether an epidemic was due to wild strains. These issues with biocontrol agents will become more acute with transgenically-enhanced biocontrol agents.

There is thus a great need for, and it would be highly advantageous to have, a database server and a method for assigning sequences to be used to genetically mark organisms and for book keeping data pertaining to the genetically marked organisms their owner, producer or source.

SUMMARY OF THE INVENTION

According to one aspect of the present invention there is provided a method of marking individuals of commercially distributed organism or organisms and offspring thereof, the method comprising the step of genetically marking a plurality of individuals of the organism or organisms with a plurality of unique DNA sequences, each of the unique DNA sequences includes a variable region, so as to produce artificial, inherited and detectable genetic variability among the plurality of individuals of the commercially distributed organism or organisms.

According to another aspect of the present invention there is provided a method of identifying individuals belonging to a commercially distributed organism, the method comprising the steps of (a) genetically marking a plurality of individuals of the organism with a plurality of unique DNA sequences, each of the unique DNA sequences includes at least one variable region; (b) providing a database server including a lookup table associating each of the plurality of individuals with one of the plurality of unique DNA sequences; and (c) identifying whether an examined individual of the organism being one of the plurality of individuals or offspring thereof, and if so, which of the plurality of individuals or offspring thereof, by (i) determining a presence or absence, and if present, a nucleotide sequence of a unique DNA sequence of the plurality of unique DNA sequences by which the examined individual being genetically marked; and (ii) identifying the examined individual by associating the nucleotide sequence to one of the plurality of individuals via the lookup table of the database server.

According to yet another aspect of the present invention there is provided an organism having a genome, the organism being genetically marked by (a) at least one unique DNA sequence which is known in public; and (b) at least one unique DNA sequence that is unknown, at least not as a genetic mark, in public.

According to still another aspect of the present invention there is provided a system for assigning DNA sequences to serve as genetic markers of commercially distributed organisms, the system comprising a database server being designed and constructed for managing a sequences database and serving for (a) assigning at least one sequence of the sequences to an assignee upon request; and (b) bookkeeping data pertaining to step (a).

According to an additional aspect of the present invention there is provided a method assigning DNA sequences to serve as genetic markers of commercially distributed organisms, the method is effected by a data processor operatively communicating with a sequences data base and comprising the steps of (a) assigning at least one sequence of the sequences to an assignee upon request; and (b) book-keeping data pertaining to step (a).

According to further features in preferred embodiments of the invention described below, the request is effected via a communications network, such as the Internet According to still further features in the described preferred embodiments the data pertaining to step (a) includes an identity of the assignee and/or an identity of an organism.

According to still further features in the described preferred embodiments the database server further serves for debiting the assignee and the method further comprising the step of debiting the assignee.

According to still further features in the described preferred embodiments each of the sequences includes a variable region. Preferably, each of the sequences includes a pair of universal regions, one on each side of the variable region.

According to still further features in the described preferred embodiments the database server further serves for (i) receiving a sequence input from a user and comparing the sequence input to sequences of the sequences database which have already been assigned; and, if no matching sequence is found (ii) identifying the user as an assignee of the sequence input. Thus, the method further comprising the steps of (c) receiving a sequence input from a user and comparing the sequence input to sequences of the sequences database which have already been assigned; and, if no matching sequence is found; (d) identifying the user as an assignee of the sequence input.

According to still further features in the described preferred embodiments the system further comprising a DNA synthesizer being in data communication with the database server, the DNA synthesizer serving for automatically synthesizing assigned sequences. The method, thus, further comprising the step of communicating assigned sequences to a DNA synthesizer.

According to still further features in the described preferred embodiments the database server includes an application selected from the group consisting of (i) determining sequence identity; (ii) determining sequence homology and degree thereof; (iii) generating artificial sequences; (iv) combining sequences of different origins; (v) generating random sequences; (vi) evaluating a coding potential of a sequence; and (vii) scoring a coding potential of a sequence.

According to another aspect of the present invention there is provided a kit for marking individuals of commercially distributed organism or organisms and offspring thereof, the kit comprising a plurality of containers containing a plurality of DNA molecules, each of the DNA molecules having a variable region being flanked by a pair of universal regions. The kit preferably further comprising, in a separate container, at least one amplification primer being hybridizable to the universal regions, so as to enable amplification of the variable region of each of the DNA molecules. Additional components of the kit may include reagents required for PCR amplification. Preferably, each of the DNA molecules forms a part of a vector.

The present invention successfully addresses the shortcomings of the presently known configurations by providing a database server and a method for assigning sequences to be used to genetically mark organisms and for book keeping data pertaining to the genetically marked organisms their owner, producer or source.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
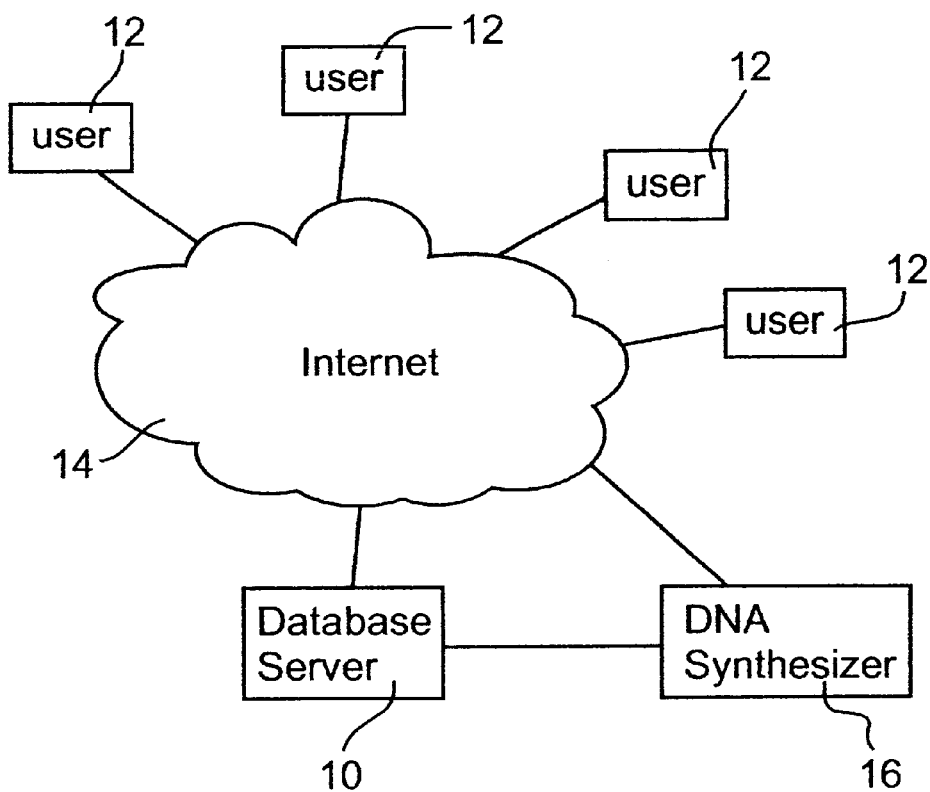
FIG. 1 is a simplified depiction of a system according to the present invention.

The present invention is of a method and system which can be used for identifying commercially distributed organisms and/or offspring thereof. Specifically, the present invention provides a database server and a method for assigning sequences to be used to genetically mark organisms and for book keeping data pertaining to the genetically marked organisms and/or their owner, producer or source.

The principles and operation of a system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In one aspect the present invention provides a system and method for assigning DNA sequences to serve as genetic markers of commercially distributed organisms. As shown in FIG. 1, the system according to this aspect of the invention includes a database server 10 which includes a data processor, is designed and constructed for managing a sequences database and which serves for (a) assigning at least one sequence of the sequences of the database to an assignee upon request; and (b) book-keeping data pertaining to step (a), data such as, but not limited to, particulars including the identity of the assignee and/or of an organism to be genetically marked.

Methods of inserting specific DNA sequences at one or more locations, at random or in a targeted fashion to genomes of prokaryotes or eukaryotes, unicellular or multicellular organisms, including, but not limited to, plants, such as crop plants, bacteria, fungi, insects and higher animals, including, domesticated animals and live stock, are well known in the art. Such methods which are known as, or employ steps of, transformation, transfection, trangenization, bombardment and the like, are extensively described in the scientific literature and in laboratory manuals such as, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); "Cell Biology: A Laboratory Handbook", Volumes I–III Cellis, J. E., ed. (1994);

"Culture of Animal Cells—A Manual of Basic Technique" by Freshney, Wiley-Liss, N.Y. (1994), Third Edition; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "A Practical Guide to Molecular Cloning" Perbal, B., (1984);

"PCR Protocols: A Guide To Methods And Applications", Academic Press, San Diego, Calif. (1990); all of which are incorporated by reference as if fully set forth herein.

Presently preferred characteristics of DNA sequences which are used according to the present invention to genetically mark and thereafter identify the organisms or their offspring are described in the following paragraphs.

The term "genetic mark" is used herein distinctively from the common term "genetic marker". While the latter term refers to naturally occurring genetic variations among individuals in a population, the term genetic mark as used herein specifically refers to artificial (man generated), inherited and detectable genetic variability.

In order to serve as genetic marks, DNA segments must have (i) a sequence which is appropriate (e.g., unique) to the genome of the organism in which it is present; and (ii) sequence variability, so as to enable the identification of different individuals of the organism.

With the advent of the polymerase chain reaction (PCR) technology and other amplification methods, it is nowadays relatively simple to determine the presence, absence and sequence of selected regions in genomes of organisms, provided that a sequence to be determined is either known or that regions flanking it from either side are known. Since sequence variability is required according to the present invention to produce specific identity, from a practical point of view, a DNA sequence which is used according to the present invention to genetically mark an organism preferably includes the variable region flanked by a pair of common or universal regions. Thus, amplification primers which can hybridize with the universal regions of the mark can be used with PCR to amplify the variable region and its sequence can thereafter be determined. To prevent coamplification of sequences of the genome of the organism, the variable and in particular, the common regions of a genetic mark according to the present invention are selected unique to the genome of the organism of choice, or preferably to a genus, family, order or kingdom of organisms to which the organism of choice classifies.

In addition, in order to prevent the possibility that the introduction of a genetic mark according to the present invention will result in expression of whatever genetic information encoded thereby, it is advantageous to select the variable and universal regions of the mark to be "non-sense" sequences, i.e., sequences that do not include an "open reading frame". To ensure that this is indeed the case, stop codons are preferably introduced into the sequences in all reading frames in predetermined intervals, e.g., every 2 to 20 codons.

In addition, it may be desired that the nucleotide repertoire used in a genetic mark of the present invention will be similar to the nucleotides repertoire characterizing the organism of choice. Thus, for example, for an organism having an AT rich genome, a similarly AT rich genetic mark will be employed, especially in the variable region of the genetic mark, whereas for an organism having a GC rich genome, a similarly GC rich genetic mark will be employed.

Furthermore, the degree of sequence variability among genetic marks of the present invention should be set such that even if one or several mutations are introduced thereto along generations, still mark identity is maintained. This is especially true for organisms characterized by high reproduction rates, such as bacteria. Variability of at least 1–5% among marks would typically suffice for marks of about 1000 bp. Higher percentage should be used for shorter marks.

Figure 2:
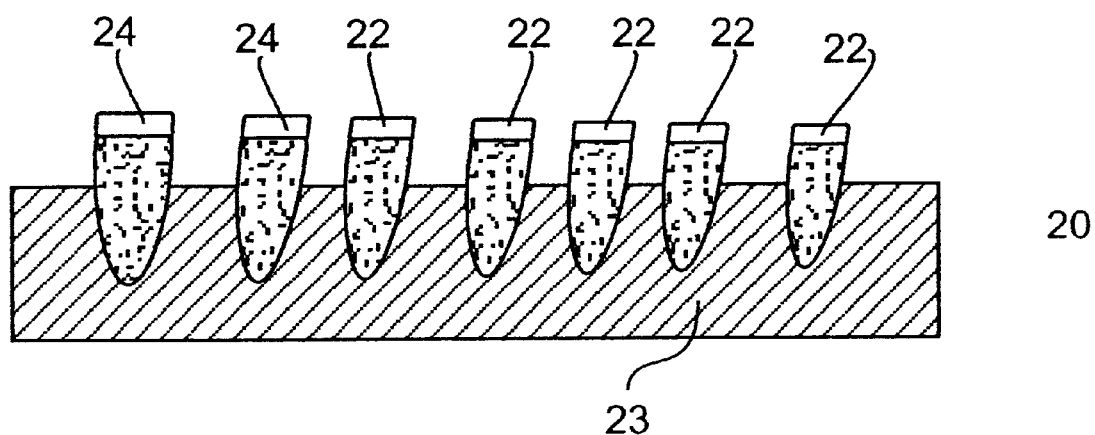
FIG. 2 is a side view of a kit according to the present invention.

Genetic marks of the present invention may be provided to users in contained in dedicated kits. As shown in FIG. 2, according to another aspect of the present invention there is provided a kit 20 for marking individuals of commercially distributed organism or organisms and offspring thereof. Kit 20 includes a plurality of containers 22 held in a suitable rack 23. Containers 22 contain a plurality of DNA molecules, each of the DNA molecules is characterized by a variable region flanked by a pair of universal (common) regions. The kit preferably further includes, in at least one separate container 24, at least one amplification primer which is hybridizable to the universal regions, so as to enable amplification of the variable region of each of the DNA molecules. Additional components of the kit may include reagents required for PCR amplification, such as, but not limited to, a concentrated (e.g., 10×) PCR buffer, a thermostable DNA polymerase, such as, but not limited to, thermophilus aquaticus (Taq) DNA polymerase and the four nucleoside tri phosphates (dNTPs). Preferably, each of the DNA molecules forms a part of a vector, which can be a plasmid, a viral vector, a cosmid, a bacmid and the like. Viral packaging reagents may also be included in the kit. Each of the containers of the kit is identified for its content. In particular, the sequence of each of the DNA molecules contained in the kit is identified directly or by a code referring to a list of sequences which is either provided with the kit or otherwise made available to the user.

A genetic mark may be cointegrated into a locus of the genome of an organism along with additional genetic material which is used to genetically modify the organism. This can be achieved either by using a single vector for introducing the mark and the additional genetic material or by employing cotransformation by two independent vectors, which, in most cases, results in a shared integration site.

As is further shown in FIG. 1, a request by a user 12 for a sequence is effected, according to a preferred embodiment of the present invention via a communications network 14, such as, but not limited to, the Internet.

For purposes of this specification and the accompanying claims, the term "user" or "user client" generally refers to a computer and includes, but is not limited to, personal computers (PC) having an operating system such as DOS, Windows™, OS/2™ or Linux; Macintosh™ computers; computers having JAVA™ -OS as the operating system; and graphical workstations such as the computers of Sun Microsystems™ and Silicon Graphics™, and other computers having some version of the UNIX operating system such as AIX™ or SOLARIS™ of Sun Microsystems ™; or any other known and available operating system; personal digital assistants (PDA), cellular telephones having Internet browsing capabilities and Web TVs.

For purposes of this specification and the accompanying claims, the term "Windows™" includes, but is not limited to, Windows2000™ Windows95™, Windows 3.x™ in which "x" is an integer such as "1", Windows NT™, Windows98™, Windows CE™ and any upgraded versions of these operating systems by Microsoft Corp. (USA).

For purposes of this specification and the accompanying claims, the term "database server" refers to any computing device or a plurality thereof acting in concert, capable of transferring, or serving, at least one electronic file to at least one other computing device.

For purposes of this specification and the accompanying claims, the term "database server" refers to any computing device capable of data processing.

For purposes of this specification and the accompanying claims, "server" and "user client" are indications of function rather than specific hardware configurations.

For purposes of this specification and the accompanying claims, the term "communications" refers to any means of information transfer, including, but not limited to, a telephone connection, a cellular telephone connection, an Internet connection, an Extranet connection, a satellite connection, cables connection, a local area network connection or a radio connection, or any other wired or unwired connection or any combination thereof.

In a preferred embodiment of the present invention, database server 10 also serves for debiting the assignee for services provided thereto. Such services, include, as is mentioned hereinabove, the provision of unique sequence or sequences and the registry thereof as being associated with the assignee, etc. Debiting capabilities over the net are well known in the art and can be obtained by our sourcing from any one of a plurality of debiting service providers, which also provide for the security required for the execution of debiting.

In some cases, a user may desire to design his own unique sequence and deposit that sequence in a depository, so as to prevent a case where a another party will use the same sequence as a genetic mark. To this end, database server 10 preferably further serves for (i) receiving a sequence input from a user and comparing the sequence input to sequences of the sequences database which have already been assigned; and, if no matching sequence is found (ii) identifying the user as an assignee of the sequence input.

Assignment of sequences according to the present invention may be of virtual sequences, i.e., their letter presentation, which can be used by the assignee to synthesize a molecule corresponding to the virtual sequence. Preferably, assignment of sequences according to the present invention is accompanied by provision of an actual DNA molecule to be used by the assignee in the process of marking an organism. To this end, the system of the present invention further includes a DNA synthesizer 16 in data communication with database server 10. DNA synthesizer 16 serves for automatically synthesizing assigned sequences.

Synthesized sequences may then be shipped directly to the assignee or may be further processed using techniques such as restriction and ligation so as to be included in a vector which is adapted to introduce an assigned sequence into the genome of an organism to be genetically marked. Such further processing can also be executed using automated machinery, such that packaging, labeling and shipment procedures are all executed without direct man intervention. It will be appreciated that DNA synthesizer 16 need not be in proximity to database server 10, as the data communication therebeween can be effected via any suitable communications network including the Internet, Intranet, Extranet, local area network, etc.

As used herein the term "DNA synthesizer" refers to a complex machinery which stores suitable chemicals and is capable of solid phase synthesis of oligonucleotides. DNA synthesizers and the chemistry of oligonucleotide synthesis are well known in the art. To this end, see, for example, "Oligonucleotide Synthesis" Gait, M. J., ed. (1984).

Efficiently managing sequence depository data which will comply with the requirements imposed by the present invention, that is to ensure that a given sequence is assigned only once and further that the identity of an assignee or organism is associated with the appropriate sequences, calls for certain sequence management capabilities, such as, but not limited to, (i) determining sequence identity; (ii) determining sequence homology and degree thereof; (iii) generating artificial sequences; (iv) combining sequences of different origins; (v) generating random sequences; (vi) evaluating a coding potential of a sequence; (vii) scoring a coding potential of a sequence and the like. Such computational functions are well known in the art and can be readily integrated into a comprehensive system acting in concert to serve registry functions as herein described.

Thus, according to the present invention there is provided a method of marking individuals of commercially distributed organism or organisms and offspring thereof. The method according to the present invention is effected by genetically marking a plurality of individuals of the organism or organisms with a plurality of unique DNA sequences, each of the unique DNA sequences includes a variable region, so as to produce artificial, inherited and detectable genetic variability among the plurality of individuals of the commercially distributed organism or organisms.

Also according to the present invention there is provided a method of identifying individuals belonging to a commercially distributed organism. The method is effected by (a) genetically marking a plurality of individuals of the organism with a plurality of unique DNA sequences, each of the unique DNA sequences includes at least one variable region; (b) providing a database server including a lookup table associating each of the plurality of individuals with one of the plurality of unique DNA sequences; and (c) identifying whether an examined individual of the organism being one of the plurality of individuals or offspring thereof, and if so, which of the plurality of individuals or offspring thereof, by (i) determining a presence or absence, and if present, a nucleotide sequence of a unique DNA sequence of the plurality of unique DNA sequences by which the examined individual being genetically marked; and (ii) identifying the examined individual by associating the nucleotide sequence to one of the plurality of individuals via the lookup table of the database server.

For some, e.g., regulatory, purposes it may be desired to mark commercially distributed organisms with publicly known marks, so as to enable regulatory authorities to readily identify the mark, and, by using the system and method of the invention, to identify the manufacturer, distributor, owner or user of the marked organism. For other purposes secrecy may be advantageous. The latter is true, for example, for preventing an attempt to genetically modify the genetic mark of a supreme strain protected by intellectual property laws. Thus, according to a preferred embodiment of the present invention, database server 10 is constructed and designed so as to enable unlimited access to some of the data stored thereby and to restrict access to classified data stored thereby to authorized users only. Methods of achieving same are well known in the art.

An intellectual property protected organism which is also subject to regulation will therefore be, according to a useful embodiment of the present invention, genetically marked by (a) at least one unique DNA sequence which is known in public; and (b) at least one unique DNA sequence that is unknown, at least not as a genetic mark, in public.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of marking a plurality of individuals of commercially distributed multicellular organisms having a plurality of different genetic backgrounds, and offspring thereof, the method comprising:

genetically marking one of a plurality of individuals of the multicellular organisms having the different genetic backgrounds with one of a plurality of unique DNA sequences, each of said unique DNA sequences comprising a variable region, so as to produce artificial, inherited and detectable genetic variability among said plurality of individuals of the commercially distributed multicellular organism; and create bookeeping data pertaining to said artificial, inherited and detectable genetic variability of said multicellular organisms and/or their owner, producer or source.

2. The method of claim 1, wherein said plurality of individuals of said commercially distributed multicellular organisms having said plurality of different genetic backgrounds are of a single species.

3. The method of claim 1, wherein said plurality of individuals of said commercially distributed multicellular organisms having said plurality of different genetic backgrounds are of a plurality of species.

4. The method of claim 1, wherein said genetically marking is by integration of said unique DNA sequences into genomes of the commercially distributed multicellular organisms.

5. The method of claim 1, wherein each of said unique DNA sequences further comprises a pair of universal regions one on each side of said variable region.

6. The method of claim 1, wherein said variable region of each of said unique DNA sequences is a non-coding sequence having a stop codon every 2 to 20 codons.

7. The method of claim 6, wherein said non-coding sequence comprises at least one stop codon in each reading frame thereof.

8. A method of marking a plurality of individuals of commercially distributed multicellular organisms, and offspring thereof, the method comprising: marking one of a plurality of individuals of the multicellular organisms with one of a plurality of unique DNA sequences, each of said unique DNA sequences comprising a variable region, so as to produce artificial, inherited and detectable genetic variability among said plurality of individuals of the commercially distributed multicellular organism; and create bookeeping data pertaining to said artificial, inherited and detectable genetic variability of said multicellular organisms and/or their owner, producer or source.

9. The method of claim 8, wherein said genetically geneticacllt making is by integration of said unique DNA sequences into genomes of the commercially distributed multicellular organisms.

10. The method of claim 8, wherein each of said unique DNA sequences further comprises a pair of universal regions one on each side of said variable region.

11. The method of claim 8, wherein said variable region of each of said unique DNA sequences is a non-coding sequence having a stop codon every 2 to 20 codons.

12. The method of claim 11, wherein said non-coding sequence comprises at least one stop codon in each reading frame thereof.

13. A method of marking a plurality of individuals of commercially distributed organisms, and offspring thereof; the method comprising:

genetically marking one of a plurality of individuals of the organisms with one of a plurality of unique DNA sequences, each of said unique DNA sequences comprising a variable region, so as to produce artificial, inherited and detectable genetic variability among said plurality of individuals of the commercially distributed organism, wherein said variable region of each of said unique DNA sequences is a non-coding sequence having a stop codon every 2 to 20 codons, whereas said genetically marking is by integration of said unique DNA sequences into genomes of the commercially distributed organisms; and create bookeeping data pertaining, to said artificial, inherited and detectable genetic variability of said organisms and/or their owner, producer or source.

14. The method of claim 13, wherein said plurality of individuals of the organisms have a plurality of different genetic backgrounds.

15. The method of claim 14, wherein said plurality of individuals of said commercially distributed organisms having said plurality of different genetic backgrounds are of a single species.

16. The method of claim 14, wherein said plurality of individuals of said commercially distributed organisms having said plurality of different genetic backgrounds arc of a plurality of species.

17. The method of claim 13, wherein each of said unique DNA sequences further comprises a pair of universal regions one on each side of said variable region.

18. The method of claim 13, wherein said non-coding sequence comprises at least one stop codon in each reading Same thereof.

19. A kit for marking individuals of commercially distributed organism or organisms and offspring thereof, the kit comprising a plurality of containers containing a plurality of DNA molecules, each of said DNA molecules including a variable region being flanked by a pair of universal regions and sequence regions being selected for integration of each of said DNA molecules into a genome of the commercially distributed organism, said variable region of cach of said unique DNA molecules being a non-coding sequence having a stop codon every 2 to 20 codons.

* * * * *